United States Patent [19]

Frigato

[11] 4,160,946
[45] Jul. 10, 1979

[54] DEVICE FOR MEASURING CONDUCTIVITY OF A SOLUTION

[75] Inventor: Giovanni Frigato, Medolla, Italy
[73] Assignee: Sandoz Ltd., Basel, Switzerland
[21] Appl. No.: 731,668
[22] Filed: Oct. 13, 1976
[30] Foreign Application Priority Data
Oct. 14, 1975 [IT] Italy ............................. 69553 A/75
[51] Int. Cl.² ............................................. G01N 27/42
[52] U.S. Cl. .................................. 324/30 R; 324/30 B
[58] Field of Search .............. 324/29, 30 R, 30 A, 324/30 B; 340/248 D

[56] References Cited
U.S. PATENT DOCUMENTS

| 3,432,418 | 3/1969 | Kleiss | 324/29 |
|---|---|---|---|
| 3,832,629 | 8/1974 | Cernek | 324/29.5 |
| 3,906,353 | 9/1975 | Murdock | 324/30 R |
| 3,922,598 | 11/1975 | Steuer | 324/30 R |
| 4,004,223 | 1/1977 | Cohen | 324/62 |

Primary Examiner—M. Tokar
Attorney, Agent, or Firm—Gerald D. Sharkin; Robert S. Honor; Walter F. Jewell

[57] ABSTRACT

The invention concerns a novel device for measuring the conductivity of a solution, comprising a probe having at least two electrodes for immersion in the solution, and converter means for converting the output from the electrodes which is proportional to the conductivity of the solution into an output having a frequency which is proportional to said conductivity. The converter means may comprise a difference amplifier operating as an oscillator.

3 Claims, 2 Drawing Figures

DEVICE FOR MEASURING CONDUCTIVITY OF A SOLUTION

The invention relates to a device for measuring the conductivity of a solution. More particularly, the invention concerns a device for measuring the conductivity of a solution to thus provide an indirect measurement of the concentration of salts in a solution.

The concentration of salts in a solution can be measured indirectly by measuring of the conductivity of the solution, the measurement of conductivity being obtained by measuring the conductance of the solution.

The conductance of the solution can be measured by means of a probe immersed in the solution, usually comprising one or more electrodes forming a twin electrode of opposite polarity, which is disposed in an arm of a bridge circuit including a direct current supply source. An output from the bridge which may be measured is that which is dependent on the conductance of the solution. Such a measurement, however, is subject to various errors, mainly because the geometrical dimensions of the electrodes forming the twin electrode are not perfectly identical for different probes. This results in variations in the constant for coverting conductance to conductivity. Furthermore, if the electrodes in the twin electrode are disposed at a distance from the bridge circuit and connected thereto by a cable, considerable interference can be caused by interfering parameters of the cable which distort the measurement. In addition, the conductivity the solution varies with temperature and such variations need to be compensated to avoid errors in measurements of concentration.

Various methods have been employed for reducing errors in measurement. For example, in order to avoid errors due to differences in the geometrical dimensions of the electrodes, each probe has been callibrated with the aid of a separate calibrating instrument. In this method, each probe needs to be calibrated and extreme care has to be taken to avoid errors when coupling the probe to the calibrating instrument. In order to compensate variations of the conductivity of the solution with temperature, two methods are adopted, viz. either the probe is coupled to a calculator circuit which records the conductivity and temperature of the solution and provides the correct value, or the probe is associated with a thermistor immersed in the solution.

The above methods for correcting measurements of conductivity are complex and costly or not sufficiently reliable, and it is an object of the invention to provide a device of simple and relatively inexpensive construction for measuring the conductivity and thus the concentration of salts in a solution which provides a reading which is substantially free from the aforementioned type of errors.

More particularly, an object of the invention is to provide a device of the aforementioned kind which is particularly suitable for measuring conductance and hence conductivity of dialysis liquid at a temperature of about 25° C.

The invention provides a device for measuring the conductivity of a solution, comprising a probe having at least two electrodes for immersion in the solution, and converter means for converting the output from the electrodes which is proportional to the conductivity of the solution into an output having a frequency proportional to said conductivity.

The invention will be more clearly understood from the following description of an embodiment with reference to the accompanying drawings in which:

FIG. 1 shows a group of electrodes 10 which are immersed in a solution, the conductivity concentration of which is to be measured.

Figure 1:
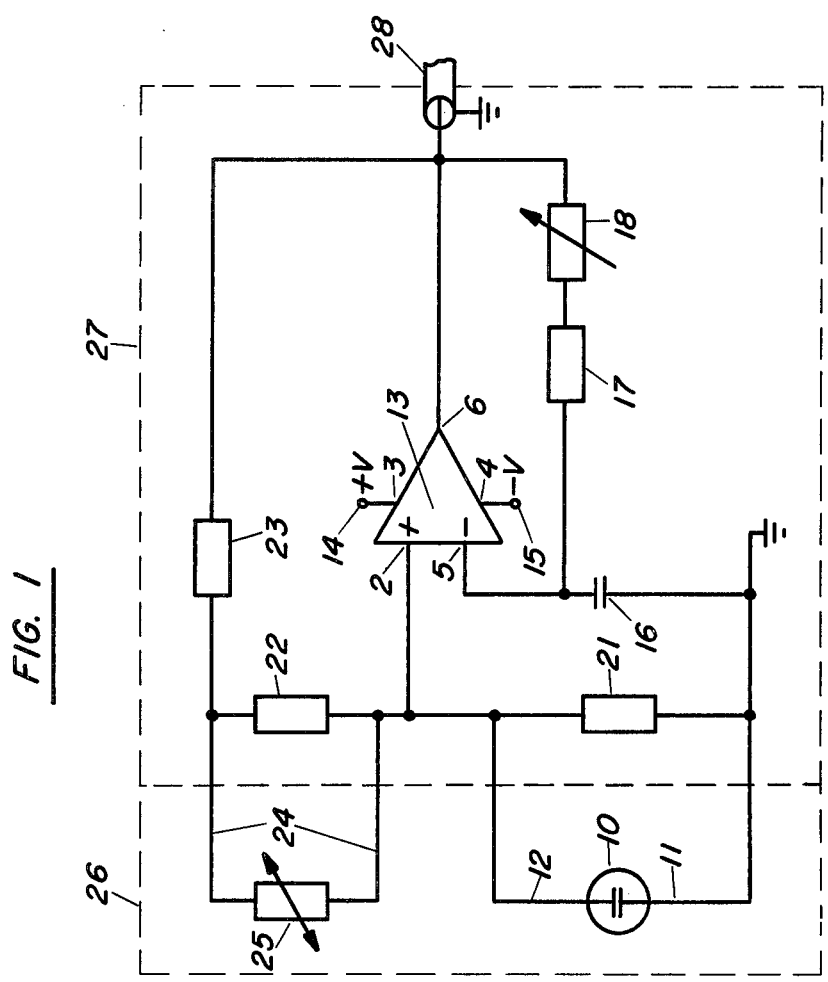
FIG. 1 shows an electronic circuit of a device in accordance with the invention.

The group of electrodes 10 form a twin electrode of opposite polarity having two end connections 11 and 12, the first of which is connected to earth and the second of which leads to an non-inverting input 2 of a difference amplifier 13. The amplifier has two supply inputs 3 and 4, an inverting input 5, and an output 6.

The supply inputs 3 and 4, are respectively connected to terminals 14 and 15, across which a voltage of $+V$ and $-V$ is respectively applied. A capacitor 16 is connected between earth and the inverting input 5, and a resistor 17 of fixed value and a variable resistor 18 are arranged in series between input 5 and output 6.

A resistor 21 is connected between the non-inverting input 2 and earth, i.e. in parallel with the electrode group 10. Two resistors 22 and 23 are provided in series between input 2 and output 6 and a thermistor 25 is connected in parallel with resistor 22, through connections 24. The group of electrodes 10, thermistor 25 and connections 11, 12 and 24 are comprised in that portion 26 of the device which is for being immersed in the solution, whereas the other components are comprised in portion 27.

A connecting coaxial cable 28 leads out from output 6.

Figure 2:
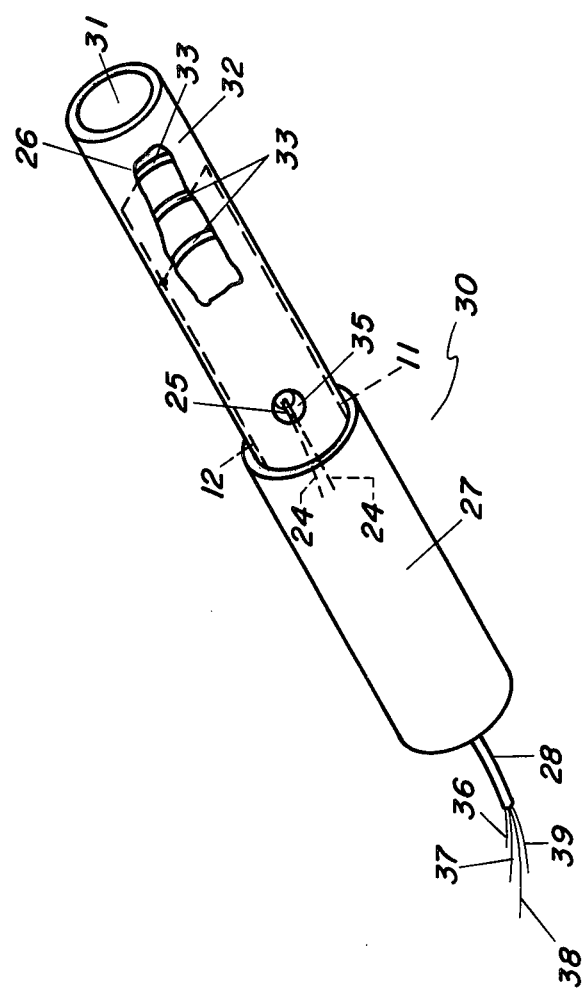
FIG. 2 is a perspective view, partly cut away, of the probe comprised in the invention.

FIG. 2 shows a complete probe 30 comprising portions 26 and 27, each of which is cylindrical in shape. Portion 26 has an axial orifice 31 bounded by an annular wall 32. Three substantially equidistant graphite rings 33 are located in wall 32 and contact with its inner surface, forming the group of electrodes 10. The end rings 33 are electrically connected to one another and to portion 27 by connection 12. The central ring 33, on the other hand, is connected to portion 27 via connection 11. An aperture 35 is provided towards the end of part 6 near the portion 27. The thermistor 25 is located in aperture 35, which is connected to part 27 through connections 24. The other components (not shown) described in FIG. 1 are located in portion 27; after they have been introduced into portion 27 they can suitably sealed with resin by conventional means. Cable 28 extends from the bottom end of part 27 and has four conductors 36, 37, 38, 39 for connection respectively to the supply terminals 14 and 15, the output 6 and earth.

With reference to the diagram in FIG. 1, data of the components of an exemplary embodiment which have been found to operate satisfactorily in practice are as follows:

| Resistors | | | Capacitors | |
|---|---|---|---|---|
| 17 | 56 | KΩ | 16 | 0.015 μ F |
| 18 | 50 | KΩ | | |
| 23 | 1250 | Ω | | Thermistor |
| 22 | 9 | KΩ | 25 | Fenwall Type UUA 32J3 |
| 21 | 10 | KΩ | | from 2252Ω at 25° C. |
| Difference amplifier | | | Supply voltage | |
| 13 | | μa 709 | | ± V = ± 15 volt |

The difference amplifier 13 in the circuit shown in FIG. 1 functions as an oscillator producing a periodic square-wave signal at output 6.

If $R_F$ is the sum of the resistances of resistors 17 and 18,

C is the capacitance of capacitor 16, $R_C$ is the resistance of electrode group 10 in parallel with resistor 21 (this resistance, however, is substantially equal to that of electrode group 10, since the resistor 21 of much higher resistance is employed only to reduce polarisation of electrode group 10 to negligible levels) and $R_T$ is the sum of the resistance of resistor 23 and the resistance of resistor 22 and thermistor 25 in parallel, it is clear, by known calculation, that the frequency of the periodic square wave at output 6 is:

$$F = \frac{1}{2 R_F C \ln(2 \frac{R_C}{R_T} + 1)}$$

Accordingly, the frequency F is proportional to $1/R_F C$, to $1/R_C$, apart from non-linearity factors and to $R_T$, also due to non-linearity factors. Accordingly, if portion 26 of probe 39 is placed in a solution of which the concentration is to be measured and if the volatge $\pm V$ is supplied to terminals 4 and 15 through cable 28, a periodic wave output appears at output 6 which has a frequency proportional to $1/R_C$ (the non-linearity factors are practically negligible in a relatively restricted measuring region such as a dialysis bath); consquently the wave is proportional to the conductance of the solution. The output signal can be sent along conductor 38 of cable 28 to a suitable frequency-measuring apparatus which, by means of a suitably-calibrated scale, can indicate the conductivity or concentration of the solution. The value of the frequency (proportional to $1/R_F C$) can be adjusted by adjusting the variable resistors 18; advantageously the frequency value may be made to coincide with the conductivity value on a suitable scale. The frequency in any case needs to be sufficiently low for the switching times of difference amplifier 13 to be negligible. Accordingly, the probe according to the invention converts the output from electrode group 10, which has a value proportional to the conductivity of the solution, into an output at 6 whose frequency is proportional to the aforementioned conductivity. Since the frequency is a substantially constant parameter in transmission, the output can be sent to recording and operating circuits, even at considerable distances, without being effected by interfering parameters and thus without error, distorion and non-linearity. The recording circuits can be conventional digital frequency-meters, which can also indicate the conductivity or concentration of the solution directly in visual form. Alternatively, the circuits can convert the frequency into a voltage proportional to the frequency which can be applied across a device for controlling and monitoring the concentration of the solution.

In view of their different geometrical dimensions, the different outputs obtained from the various electrode groups can be referred to a single common frequency value at output 6, having the same calibration as the variable resistor 18, which may be adjustable from the bottom of portion 27 of probe 30. This obviates the need to associate each probe with an individual measuring instrument, and different probes can easily be interchanged.

Finally, in order to obviate the disadvantage of errors in the concentration reading due to variations in the conductivity of the solution with temperature, the variations in conductivity are compensated by thermistor 25, which varies the $R_T$ value in accordance with the following formula:

$$R_T \times \text{conductivity} = R_{constant} \times \text{conductivity at 25° C.}$$

The maximum permitted error is 1%.

Accordingly, the circuit described in FIG. 1 having the said value is adapted to record the equivalent conductivity at 25° C. (14.1 mS/cm) and thus record the concentration of dialysis liquid at a bath temperature anywhere between 5° and 45° C., with a maximum error of less than 1%.

Accordingly, the frequency value at output 6 is substantially constant in spite of variations in the temperature of the solution, and indicates the concentration independently of the temperature.

The device according to the invention has numerous advantages; more particularly the conductivity and/or concentration can be measured at a considerable distance away from the measuring site without introducing errors. There is complete accuracy and reproducibility between different probes, particularly since the reading is not influenced by variations in the temperature of the solution.

The device is relatively simple and inexpensive, provides highly accurate and reliable measurement, and the output can be interpreted and measured with the aid of conventional commercial measuring devices (frequency-meters). In addition, the circuit consumes little power and is extremely insensitive to variations in the temperature or supply voltage and can thus operate with portable battery-powered circuits.

The described embodiment can be changed without departing from the invention. For example, thermistor 25 can be a fixed resistor if it is desired to obtain an output at 6 which is proportional to the conductivity of the solution at all temperatures. Similarly, in order to determine the concentration of a different type of solution, over a different range of values from that used for dialysis liquid, variations can be made in the values given for the components, more particularly in the resistors 22 and 23 associated with the thermistor 25.

I claim:

1. A device for measuring the conductivity of a solution, comprising a single elongated probe having at least two electrodes of opposite polarity exposed at its free end for immersion in the solution, and converter means comprising one single difference amplifier operating as an oscillator for converting the output from the electrodes which is proportional to the conductivity of the solution into an output having a frequency which is proportional to said conductivity, the amplifier having two supply inputs, a noninverting input, an inverting input and an output, the output from the one electrode being connected to the non-inverting input of the amplifier and the other electrode being earthed, the output for measurement being that taken from the output of the amplifier, and first and second feedback networks provided between the output of the difference amplifier and the two inputs, in which a variable resistor for adjusting the frequency of the output from the amplifier is included in the first of said networks.

2. A device according to claim 1 in which a thermistor for compensating the variation in the conductivity of the solution with temperature is provided in the second of said networks, so that a preset frequency of the output from the amplifier remains constant in spite of variations in the temperature of the solution.

3. A device according to claim 1, in which the preset frequency is the frequency proportional to the conductivity of the solution at a temperature of 25° C.

* * * * *